United States Patent [19]

Kloehn et al.

[11] Patent Number: 4,573,382
[45] Date of Patent: Mar. 4, 1986

[54] APPARATUS AND METHOD FOR CUTTING A WEB

[75] Inventors: Kurt J. Kloehn, Outagamie County; Gregory J. Rajala, Winnebago County; Kent W. Abel, Outagamie County, all of Wis.

[73] Assignee: Kimberly-Clark Corporation, Neenah, Wis.

[21] Appl. No.: 607,496

[22] Filed: May 7, 1984

[51] Int. Cl.[4] .............................................. B26F 3/00
[52] U.S. Cl. .......................................... 83/53; 83/177; 83/428; 83/917
[58] Field of Search ................... 83/53, 177, 428, 917

[56] References Cited

U.S. PATENT DOCUMENTS 4,007,652  2/1977  Shinomiya et al. ............. 83/177 X
4,048,885  9/1977  Miyakita ............................. 83/53 X

*Primary Examiner*—James M. Meister
*Attorney, Agent, or Firm*—H. Donald Nelson

[57] ABSTRACT

An apparatus and method for cutting a web of material having a conveyor carrying and continuously moving a length of the web material, an oscillating means, a cutting arm mounted on the oscillating means and moveable between a position over the web and a position laterally outside of the web in a turn-around area. A nozzle mounted on the cutting arm and connected to a source of high pressure fluid and a fluid jet ejected from the nozzle towards the web and moved by the cutting arm in an oscillating manner along a path between the turn-around area and the position over the web. As the fluid jet oscillates along its path, the movement of the fluid jet in conjunction with the movement of the web results in the cutting out of a section of the web.

6 Claims, 4 Drawing Figures

APPARATUS AND METHOD FOR CUTTING A WEB

FIELD OF THE INVENTION

This invention relates to an apparatus and method for cutting a web along a path which varies in angle and direction and, in particular, to an apparatus and method for cutting sections from the edge of a web for use in fabricating disposable diapers.

BACKGROUND OF THE INVENTION

In the manufacture of various types of goods utilizing flat sheet material, there is a frequent need to cut the material into sections or cut a pattern in the material. It is typically desirable to perform such cutting operations while the material is moving past a cutting mechanism at relatively high speeds. In the disposable diaper business, there has been an increase in recent years in the popularity of diapers which are shaped to fit around the legs of the wearer. This shaping is usually accomplished during the diaper manufacturing process by cutting spaced apart sections out of the side areas of the web or webs from which the diapers are fabricated. Each space in the web from which a section has been cut constitutes the shaped leg area in a finished disposable diaper.

A wide variety of cutting mechanisms have been used to accomplish the cutting of sheet materials, depending on the particular type of material and the pattern or path to be cut. Somewhat more recent types of commonly used cutting device utilizes a high velocity stream or jet of a fluid such as water. U.S. Pat. No. 4,048,885 to Miyakita et al., issued Sept. 30, 1977, and U.S. Pat. No. 4,007,652 to Shinomiya et al, issued Feb. 15, 1977, are examples of such cutting devices.

Another type of cutting apparatus of which we are aware and which is presently used by the Kimberly-Clark Corporation, the assignee of the instant application, utilizes a commercially available cam oscillating mechanism. The cam mechanism is mounted above a passing web of material. A cutting arm connected on one end to the cam mechanism extends over the web in the direction of movement of the web. The arm is moved in an oscillating manner over the web. A nozzle emitting a fluid jet cuts the web along a cutting path determined by the speed of movement and position of the cutting arm and the speed of the passing web. The positioning of the cam mechanism and the cutting arm over the web and the extension of the cutting arm in the direction of movement of the web result in an improved cutting device in comparison with previously known devices.

We have now developed an improvement to the above described cutting apparatus used by the Kimberly-Clark Corporation. We believe our improvement provides significant advantages with respect to increased speed in performing cutting operations and decreased stress on the cutting apparatus.

SUMMARY OF THE INVENTION

The apparatus and method according to the invention are carried out by providing a conveyor carrying and continuously moving a length of a web material, an oscillating means, a cutting arm mounted on the oscillating means and moveable between a position over the web and a position laterally outside of the web in a turn-around area, a nozzle mounted on the cutting arm and connected to a source of high pressure fluid, and a fluid jet ejected from the nozzle towards the web and moved by the cutting arm in an oscillating manner along a path between the turn-around area and the position over the web. As the fluid jet oscillates along its path, the movement of the fluid jet in conjunction with the movement of the web results in the tracing of a line which defines a fluid jet turn-around area while the line is laterally outside of the edge of the web and a line along which the web is cut while the fluid jet is over the web. The path of movement of the fluid jet is determined by identifying those lines following the highest pitch slope of the portions of the traced or cut lines in the turn-around area or in the web. The path of movement of the fluid jet lies substantially along a line having an angle between the angles of said slope lines relative to a common reference line. Where the highest pitch slopes occur along the traced line in the turn-around area, the line along which the path of movement of the fluid lies laterally outward of the edge of the web. Preferably, the line which the path of the fluid jet follows is an optimum line locating the cutting path of the fluid jet and is at an angle determined in accord with the equation $$\theta = \arctan 2 \left[ \frac{\tan \alpha_1 \alpha_2}{\tan \alpha_2 + \tan \alpha_1} \right]$$

where $\theta$ is the angle of the optimum line relative to a reference line and $\alpha_1$ and $\alpha_2$ are angles of slope lines relative to the same reference line. In order to locate the cutting path of the fluid jet substantially along a line oriented at an angle $\theta$ or at an angle between the angle of the slope lines, the pivot point of the cutting arm is positioned on a line perpendicular to and bisecting the angularly oriented lines.

BRIEF DESCRIPTION OF THE DRAWINGS

Further advantages of the invention will appear when taken in conjunction with the accompanying drawings, in which.

DETAILED DESCRIPTION OF THE INVENTION

Figure 1:
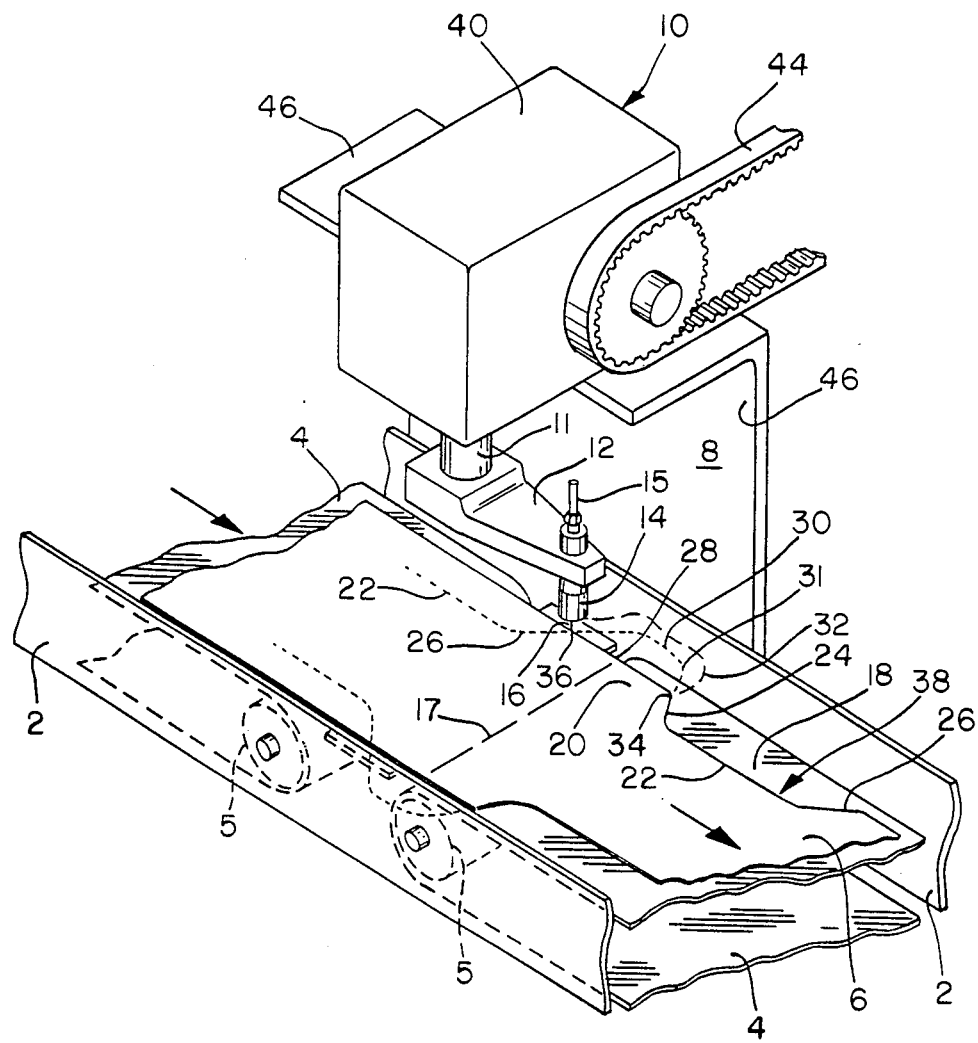
FIG. 1 is a perspective view of a cutting apparatus of the invention.

Referring to FIG. 1, the apparatus of the invention is shown as having a frame 2 on which a conveyor means 4 is mounted for continuous movement in the direction of the arrow shown adjacent the conveyor means 4. A length of web material 6 is carried on the conveyor means 4 and continuously moved by the conveyor means 4 in the direction of the conveyor movement. Movement of the conveyor means 4 is provided by suitable drive means, not shown, connected to the conveyor. A cutting means 8 is provided and includes an oscillator means 10, having an oscillating output shaft 11, a cutting arm 12 mounted on the oscillating shaft 11, and a nozzle 14 mounted on the cutting arm and moveable in an oscillatory manner over the web 6. A stream of high pressure fluid or jet 16 is emitted from the nozzle 14 toward the web material 6 and is of a sufficient energy level to cut through the web as it passes below the nozzle. The high pressure fluid is provided to the nozzle 14 through a fluid line 15 from a suitable fluid source which is not shown.

The web material is a relatively flat sheet of material and, where the web is intended for use in fabricating disposable garments such as disposable diapers, the web may comprise a fluid pervious or impervious sheet material or fluid absorbent material such as a continuous batt of cellulosic fluff. In a later step in the fabrication of diapers from the web 6, the web is cut along the dashed lines 17 to form individual web blanks 19. The cutout areas 18 illustrated in FIG. 1 will be leg areas in a completed diaper and the protruding areas 20 will be waist areas in adjacent diaper blanks 19 cut from the web 6. The cutout area 18 is defined by a straight or low curvature cut line 22 and cut lines 24 and 26. The lines 24 and 26 may be entirely curved or include a straight and curved portion and may be of similar or different shape. The protruding areas 20, include lateral edge lines 28. The cut lines 22, 26, 24 and the edge line 28 together define the lateral edge of the web along its length in the cutout and protruding areas 18 and 20, respectively. While the fluid jet 16 is laterally outward of the edge line 28 of the web 6, a line 30 is traced by the fluid jet 16 on a plane 32 which extends from and is coplaner with the web material 6 and may be considered to move with the web 6. The line 30 runs from its intersection 34 with the edge line 28 to its intersection 36 with the edge line of the web 6. As will be discussed in greater detail hereinafter, the traced line 30 is located in the turn-around area 35 of oscillatory movement of the fluid jet 16.

Figure 2:
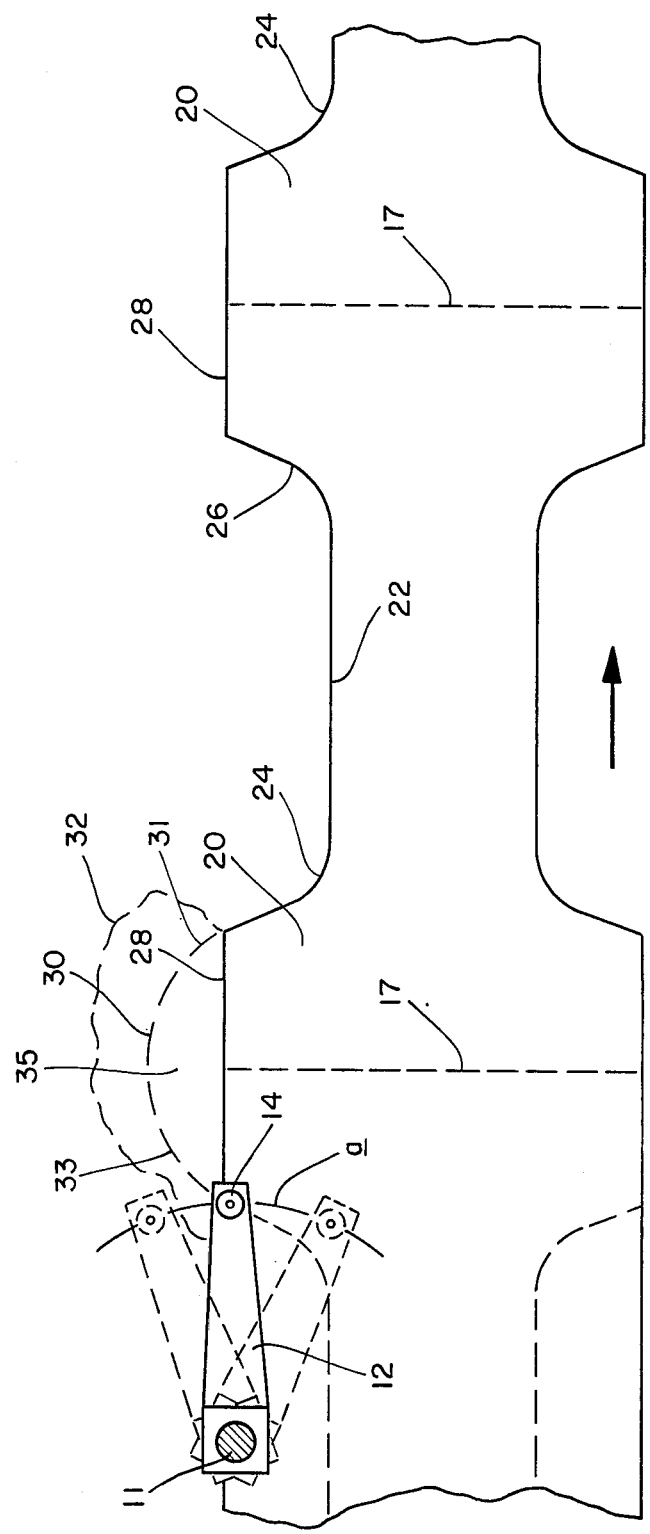
FIG. 2 is a plan view of the web being cut and a portion of the cutting apparatus during a cutting operation.

In FIG. 2, the cutting arm 12 is shown mounted on the oscillating shaft 11. The axis of the oscillating shaft 11 is the pivoting axis for the arm 12. The arm 12 is shown in full lines at a position at which the fluid jet 16 is about to initiate cutting a line 26 in the web 6. The arm 12 is also shown in phantom lines after it has moved over the web 6 to its inwardmost position where the fluid jet 16 will cut the line 22. The arm 12 is also shown in phantom lines in its outwardmost position beyond the edge line 28 of the web 6 in the turn around area 35 where the arm 12 and nozzle 14 and therefore fluid jet 16 turn around and return to the area over the web 6. As shown in FIG. 2, the path traced by the fluid jet 16, without considering the movement of the web 6 or the plane 32 below the fluid jet 16, is the arc a of a circle having a radius centered on the axis of the oscillating shaft 11 of the oscillator means 10. When the movement of the web 6 and the plane 32 is considered in conjunction with the movement of the fluid jet 16 across the plane 32 and the web 6, a pattern or line 38 is traced which comprises the cut lines 26, 22 and 24 and the traced line 30. It should be noted that since the motion of the web 6 and the oscillatory motion of the fluid jet 16 are continuous, the pattern traced by the fluid jet 16 is continuously repeated.

Considering the entire line 38 traced by the fluid jet 16, it may be seen in FIG. 2 that the cut line portions 24 and 26 and the portions of the turn-around line 30 most adjacent the edge line 28 of the web 6, have slopes which are at a high angle relative to the line of the edge 28. On the other hand, the cut line 22 and the portion of the turn-around line 30 midway between the intersections 34 and 36 of the turn-around line 30 with the edge 28 have little or no slope relative to the line of the edge 28. The significance of these slopes is that, at a high slope, the fluid jet 16 must move a relative large distance transverse of the direction of movement of the web 6 and plane 32 for a given distance of movement of the web 6 and plane 32. In low slope areas of the line 38, very little transverse movement is required of the fluid jet 16. Thus, in order for the fluid jet 16 to move the distances required in the high slope areas, its speed and therefore that of the oscillating means 10 must be quite high while the high slope areas of the line 38 are being cut or traced.

The oscillator means 10 includes a cam mechanism 40, a continuously rotating input shaft 42, an input drive means 44, and the oscillating output shaft 11. The oscillator means 10 is mounted on a bracket 46 which comprises a part of the frame 2. The cam means 40 is of a type which is well known and is commercially available from various sources such as the Commercial Cam Division of Emerson Electric Company. The velocity and acceleration requirements of the high slope portions of the line 38 on the fluid jet 16 place considerable stress on the cam means 40 as it moves the fluid jet 16 along the line 38. However, these stresses seriously limit the speed at which the web 6 can be cut and therefore it is necessary that these stresses be minimized to the extent possible.

In considering this problem, it has been found that, for any particular cut or traced line having a slope relative to the web edge line 28, the most efficient cutting line of the fluid jet 16 which minimizes stresses on the cam means 40 is a line perpendicular to the line of the slope located by the angle $\alpha$. However, where several different lines are being cut or traced by the cutting means 8 which have high pitch slopes relative to the line of the edge 28, these various lines must be taken into consideration and a compromise cutting line for the fluid jet 16 to follow must be located which is at the optimum location for the most efficient cutting of the several lines considered. The slopes which control the location of the compromise cutting line will be determined by the highest pitch lines along the entire path of the fluid jet 16.

Figure 3:
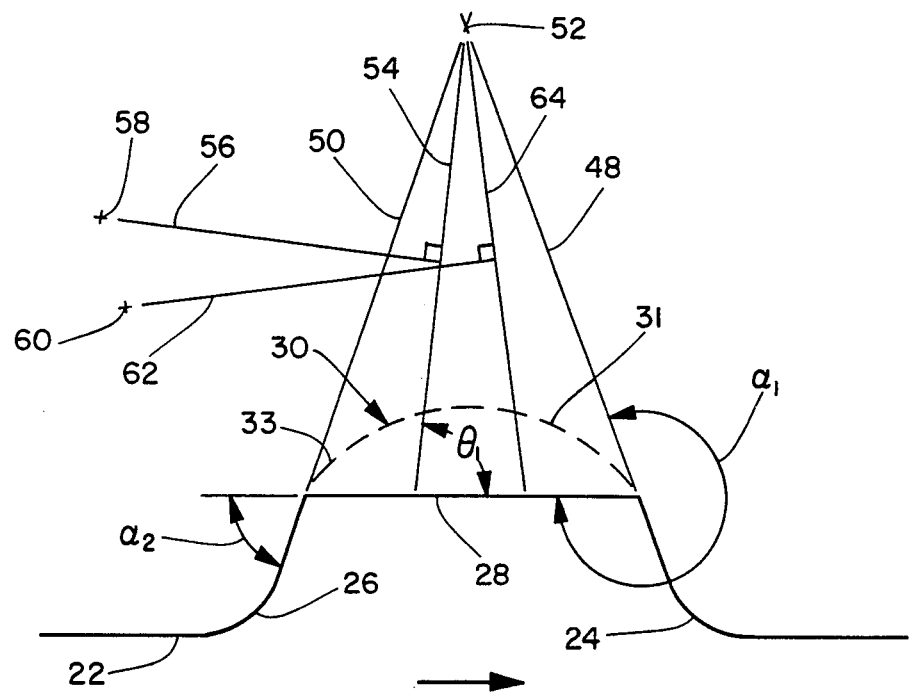
FIG. 3 illustrates the criteria locating the cutting path of the fluid jet of the cutting apparatus.

When cutting leg areas for small size disposable diapers, the acceleration, deceleration and velocity stresses in the turn-around area 35 during tracing of the line 30 by the fluid jet 16 places particularly severe stresses on the cam means 40. Thus, the optimum cutting path for the fluid jet 16 to follow must be located with reference to the traced line 30 in the turn-around area 35. To meet this requirement, the arcuate path a of the fluid jet 16 must be located along a line oriented at an angle between the angle of the lines of the highest pitch slopes, relative to the same reference line, of the traced line portions 31 and 33 of the traced line 30. As illustrated in FIG. 3, these highest pitch slopes are the slopes of the line portions 31 and 33 at or adjacent to the intersection of the traced line 30 with the edge line 28 of the web 6. A line following the highest pitch slope of the line 31 is extended away from the line portion 31 and identified by the numeral 48. A line following the highest pitch slope of the line portion 33 is extended away from the line portion 33 and identified by the numeral 50. The lines 48 and 50 may also be tangent lines where the highest pitch slope portions of the traced line 30 occur on a curve. The lines 48 and 50 intersect at a point or intersection 52. The line 54 is the line which has the desired angular orientation between the angular orientation of the lines 48 and 50 relative to line 28 and is therefore the optimum cutting line which the fluid jet should follow to be as perpendicular as possible to the high pitch slope areas of the line portions 31 and 33 while tracing the line 30 in the turn-around area 35. Consequently, locating the pivot point 58 for the pivot axis of the arm 12 at a position which will permit the fluid jet 16 to move on a cutting path a as shown in FIG. 2, substantially following the optimum cutting line 54 will result in minimum possible stresses on the cam means 40. The term "substantially" as used in this context, means that the cutting path a touches the optimum cutting line 54 at at least one point and runs generally in the direction of the line 54. The line 54 has an angle lying between the angle of the slope lines 48 and 50 and connects the intersection 52 and the edge 28 of the web 6. This requirement is met by positioning the pivot point 58 for the cutting arm 12 on a line 56 perpendicular to the optimum cutting line 54. In addition, the arm 12 must be of a sufficient length to enable the fluid jet 16 to reach and cut the inwardmost line 22 on the web 6 during the oscillating movement of the arm 12.

The angular location of the optimum cutting line 54 can be found by calculating the angle $\theta_1$, as shown in FIG. 3. In general, the angle $\theta$ is determined by the formula $$\theta = \arctan 2 \left[ \frac{\tan \alpha_1 \tan \alpha_2}{\tan \alpha_2 + \tan \alpha_1} \right]$$

where $\alpha_1$ is equal to the angle between the line of the edge 28 and the slope of a first trace or cut line and $\alpha_2$ equals the angle between the line of the edge 28 and the line following the slope of a second trace or cut line.

Figure 4:
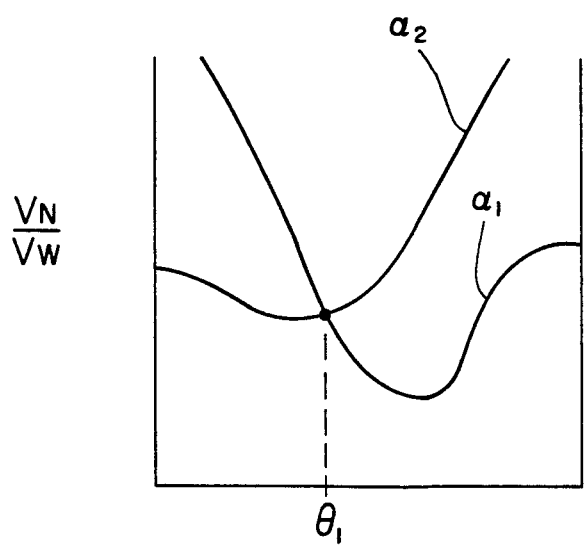
FIG. 4 is a plot of curves determining the angular orientation of an optimum line for the cutting path of the cutting apparatus.

In FIG. 4, a graph is illustrated in which the ratio ($v_N/v_W$) is determined by plotting curves for values of $\alpha_1$ and $\alpha_2$ for varying values of $\theta$. The values of ($v_N/V_W$) on the ordinate axis are determined by the equation $$v_W = \frac{1}{\cos \theta - \frac{\sin \theta}{\tan \alpha}}$$

where $v_N$ equals velocity of the nozzle and $v_W$ equals velocity of the web. The intersection of the curves for $\alpha_1$ and $\alpha_2$ determine the value of $\theta_1$. In this manner, the angular position of any optimum cutting line defining the path of the fluid jet 16 can be located.

It is further critical that the optimum cutting line 54 extend only between the intersection 52 of the lines 48 and 50 and the edge line 28 of the web 6 when the highest pitch slopes are along the line 30. As can be seen in FIG. 3, the pivot point 58 is on the perpendicular line 56 bisecting the optimum cutting line 54. Thus, defining the length of the optimum cutting line 54 to extend only between the edge line 28 and the intersection 52 directly determines the distance of the pivot point 58 from the trace line 30 and thereby the angle of the cutting path a of the fluid jet 16 relative to the line 30. Use of a length for the optimum cutting line 54 that would extend further inwardly toward the web 6 would tend to provide an optimum cutting path of travel of the fluid jet 16 for cutting the lines 26 or 24 but would diminish efficiency in tracing of the line 30 in the turn around-area 35.

Although the optimum line for locating the path a of the fluid jet 16 is optimum cutting line 54, relatively good effectiveness in reducing the stress on the cam means 40 can also be obtained by positioning the pivot point 60 of the cutting arm 12 relative to any other line oriented at an angle between the angle of the slope lines 48 and 50 relative to the same reference line and connecting the intersection 52 and the edge line 28 of web 6. Thus, a cutting line 64 may be used and the pivot point of the arm 12 is then located at point 60 on the perpendicular bisecting line 62 of line 64.

It will be understood that the foregoing description of the present invention is for purposes of illustration only and that the invention is susceptible to a number of modifications or changes, none in which entail any departure from the spirit and scope of the present invention as defined in the hereto appended claims.

What is claimed is:

1. In an apparatus for cutting a continuously moving length of web material with a high pressure fluid jet including a pivotable arm positioned above the moving web material, oscillating means having an oscillating shaft connected to the arm for moving the arm along an oscillating path between a position over the web and a position laterally outside of an edge of the web, the axis of the shaft defining the pivoting axis of the arm, and nozzle means mounted on the arm for ejecting the fluid jet through the web material to cut a section from the web material, the oscillating movement of the nozzle means from said position laterally outside the edge of the moving web to the position over the web, in conjunction with the movement of the web, resulting in the tracing of a line by the fluid jet laterally outside the web from an intersecting point with the edge of the web at a first location to an intersecting point with the edge of the web at a second location, the combination wherein:

the traced line has first and second slope lines respectively adjacent each of said first and second locations, the first slope line forming a first angle with said edge of the web and the second slope line forming a second angle with said edge of the web, the two slope lines having an intersection spaced from the web;

a cutting line positioned at an angle between said first and second angles relative to said edge of the web and extending from said edge of the web outwardly of the web;

a line perpendicular to the cutting line and bisecting the cutting line;

the pivoting axis of the arm being located on the perpendicular line; and the nozzle means being positioned on the arm a distance from the pivoting axis such that the path of the fluid jet ejected from the nozzle means substantially follows said cutting line as the arm moves in an oscillating manner whereby minimum stress is applied to the cam means during oscillating movement of the nozzle means and arm.

2. The apparatus in accord with claim 1 wherein said cutting line has an optimum angular orientation determined by the equation $$\theta = \arctan 2 \left[ \frac{\tan \alpha_1 \tan \alpha_2}{\tan \alpha_2 + \tan \alpha_1} \right]$$

wherein $\alpha_1$ = the angle between the first slope line and the edge of the web, $\alpha_2$ = the angle between the second slope line and the edge of the web,
$\theta$ = the angle between the cutting line and the edge of the web.

3. The apparatus in accord with claim 1 or 2 wherein the cutting line intersects said intersection of the slope lines.

4. The apparatus in accord with claim 1 or 2 wherein the first slope line is at the highest pitch of the trace line adjacent the first location and the second slope line is at the highest pitch of the trace line adjacent the second location.

5. In a method for cutting a continuously moving web of material with a fluid jet ejected from a nozzle comprising the steps of:

moving the fluid jet in an oscillating manner from a position over a portion of the web and across a first edge location of the web to a position laterally outside the web;

moving the nozzle from said position laterally outside the web across a second edge location of the web and over the web, the movement of the fluid jet over the web cutting a section from web and the movement of the fluid jet over a plane coplanar and moving with the web laterally outside the the web defining a continuous line connecting the two edge locations of the web; and controlling the oscillating movement of the fluid jet to follow a path substantially paralle to a cutting line located laterally outward of the web and having an angular orientation between the angular orientation of first and second straight lines following the highest pitch slope of said continuous line adjacent the first and second edges, respectively, of the web.

6. The method according to claim 5 wherein the step of controlling the oscillating movement of the fluid jet is accomplished by moving the fluid jet along an arcuate path substantially following a line angularly located by the equation $$\theta = \arctan 2 \frac{\tan \alpha_1 \tan \alpha_2}{\tan \alpha_2 + \tan \alpha_1}$$

wherein
$\alpha_1$ = the angle between the first slope line and the edge of the web,
$\alpha_2$ = the angle between the second slope line and the edge of the web,
$\theta$ = the angle between the cutting line and the edge of the web.

* * * * *

UNITED STATES PATENT AND TRADEMARK OFFICE
CERTIFICATE OF CORRECTION

PATENT NO. : 4,573,382
DATED : March 4, 1986
INVENTOR(S) : Kloehn, et al.

It is certified that error appears in the above-identified patent and that said Letters Patent are hereby corrected as shown below:

Column 5, lines 41-44, delete "$v_W =$" and substitute therefor $-- v_N = \dfrac{}{\overline{v_W}} --$.

Column 8, line 4, delete "paralle" and substitute therefor --parallel--.

Signed and Sealed this

Fifth Day of August 1986

[SEAL]

Attest:

DONALD J. QUIGG

Attesting Officer

Commissioner of Patents and Trademarks